(12) United States Patent
Koeda

(10) Patent No.: US 11,701,080 B2
(45) Date of Patent: Jul. 18, 2023

(54) RADIOGRAPHIC IMAGING DEVICE, RADIOGRAPHIC IMAGING SYSTEM, AND RECORDING MEDIUM

(71) Applicant: Konica Minolta, Inc., Tokyo (JP)

(72) Inventor: Keisuke Koeda, Higashimurayama (JP)

(73) Assignee: KONICA MINOLTA, INC., Tokyo (JP)

(*) Notice: Subject to any disclaimer, the term of this patent is extended or adjusted under 35 U.S.C. 154(b) by 0 days.

(21) Appl. No.: 17/358,355

(22) Filed: Jun. 25, 2021

(65) Prior Publication Data

US 2021/0401394 A1    Dec. 30, 2021

(30) Foreign Application Priority Data

Jun. 29, 2020  (JP) .................................. 2020-111029

(51) Int. Cl.
*A61B 6/00* (2006.01)

(52) U.S. Cl.
CPC .............. *A61B 6/542* (2013.01); *A61B 6/462* (2013.01); *A61B 6/465* (2013.01); *A61B 6/585* (2013.01)

(58) Field of Classification Search
CPC ..... A61B 6/4233; A61B 6/4283; A61B 6/462; A61B 6/465; A61B 6/542; A61B 6/585; G01T 1/20184; G01T 1/247
See application file for complete search history.

(56) References Cited

U.S. PATENT DOCUMENTS

| | | | | |
|---|---|---|---|---|
| 2011/0199523 A1* | 8/2011 | Tanabe | ..................... | H04N 5/32 348/311 |
| 2013/0343522 A1* | 12/2013 | Yoon | ........................ | H04N 5/32 250/394 |
| 2015/0164461 A1* | 6/2015 | Imamura | ................ | A61B 6/542 378/97 |
| 2015/0182182 A1* | 7/2015 | Tajima | ................... | A61B 6/542 378/189 |
| 2015/0316664 A1* | 11/2015 | Fujiyoshi | ............... | G01N 23/04 250/370.08 |
| 2016/0299239 A1* | 10/2016 | Watanabe | .............. | H04N 25/70 |
| 2017/0285189 A1* | 10/2017 | Ryu | ........................ | H04N 25/63 |
| 2018/0067215 A1* | 3/2018 | Mako | ...................... | G01T 1/247 |

(Continued)

FOREIGN PATENT DOCUMENTS

JP     2006-304210 A     11/2006

*Primary Examiner* — Dani Fox
*Assistant Examiner* — Soorena Kefayati
(74) *Attorney, Agent, or Firm* — Lucas & Mercanti, LLP

(57) ABSTRACT

Provided is a radiographic imaging device including: a first hardware processor; a sensor that includes multiple semiconductor elements arranged two-dimensionally and multiple switch elements respectively connected to the semiconductor elements; a gate driver that causes each of the switch elements of the sensor to switch between a conductive state and non-conductive state so as to release charge from each of the semiconductor elements; and a reader that performs readout of a signal value according to an amount of the charge released by the each of the semiconductor elements of the sensor. The first hardware processor sets an imaging condition that affects a dose of radiation reaching the sensor, selects a gate readout pattern according to the set imaging condition among different gate readout patterns, and drives the gate driver and the reader using the selected gate readout pattern.

13 Claims, 10 Drawing Sheets

(56) References Cited

U.S. PATENT DOCUMENTS

| | | | |
|---|---|---|---|
| 2018/0120458 A1* | 5/2018 | Nakamura | G01T 1/208 |
| 2018/0220979 A1* | 8/2018 | Kojima | A61B 6/542 |
| 2019/0145911 A1* | 5/2019 | Niwa | A61B 6/4452 |
| | | | 378/62 |
| 2019/0250109 A1* | 8/2019 | Yachi | H05G 1/26 |
| 2020/0041664 A1* | 2/2020 | Furumoto | G01N 23/083 |
| 2021/0067711 A1* | 3/2021 | Tezuka | G01T 1/2014 |

* cited by examiner

| IMAGED SITE AND BINNING NUMBER | SELECTABLE FRAME RATE | DEFAULT GATE READOUT CONTROL PATTERN (GATE PERIOD) | DEFAULT FRAME RATE |
|---|---|---|---|
| CHEST PA_BINNING 2 | ≤15fps | 100 μs | 15fps |
| CHEST PA_BINNING 1 | ≤7.5fps | 100 μs | 7.5fps |
| LUMBER LAT_BINNING 2 | ≤7.5fps | 200 μs | 7.5fps |
| LUMBER LAT_BINNING 1 | ≤3.75fps | 200 μs | 3.75fps |

RADIOGRAPHIC IMAGING DEVICE, RADIOGRAPHIC IMAGING SYSTEM, AND RECORDING MEDIUM

CROSS-REFERENCE TO RELATED APPLICATIONS

The entire disclosure of Japanese Patent Application No. 2020-111029 filed on Jun. 29, 2020 is incorporated herein by reference in its entirety.

BACKGROUND

Technological Field

The present invention relates to a radiographic imaging device, a radiographic imaging system, and a recording medium.

Description of the Related Art

In digital radiographic imaging devices, it is important to take enough time for various operations by readout circuits in order to accurately read signal values corresponding to amounts of charge from conductor elements, in regard of prevention of deterioration of the quality of radiographic images.

On the other hand, it may be necessary to shorten the time for the various operations by the readout circuits depending on the usage (for example, dynamic imaging) of a radiographic imaging device.

Therefore, conventionally, there have been disclosed techniques to control the operation time for readout of signal values.

For example, JP 2006-304210 A discloses an imaging device including a conversion layer to convert information from light or radiation into information on charges by incident light or radiation, a storage and readout circuit to store and read the converted information on charges, and a readout interval changing means to change intervals for reading intervals of time to read the information on charges.

Further, in JP 2006-304210 A, a readout interval changing means differentiates readout intervals between the imaging modes with lower and higher framerates.

SUMMARY

However, even when radiographic imaging is performed using such a technique as disclosed in JP 2006-304210 A, a radiographic image with an abnormal image quality is generated in some cases depending on the imaging conditions.

An object of the present invention is to generate a radiographic image without an abnormality in the image quality even when imaging conditions which used to cause an abnormality are set.

To achieve at least one of the abovementioned objects, a radiographic imaging device reflecting one aspect of the present invention includes a first hardware processor;

a sensor that includes multiple semiconductor elements arranged two-dimensionally and multiple switch elements respectively connected to the semiconductor elements;

a gate driver that causes each of the switch elements of the sensor to switch between a conductive state and non-conductive state so as to release charge from each of the semiconductor elements; and a reader that performs readout of a signal value according to an amount of the charge released by the each of the semiconductor elements of the sensor;

wherein the first hardware processor:
sets an imaging condition that affects a dose of radiation reaching the sensor;
selects a gate readout pattern according to the set imaging condition among different gate readout patterns; and
drives the gate driver and the reader using the selected gate readout pattern.

To achieve at least one of the abovementioned objects, a radiographic imaging system reflecting another aspect of the present invention includes:

a first hardware processor;

a sensor that includes multiple semiconductor elements arranged two-dimensionally and multiple switch elements respectively connected to the semiconductor elements;

a gate driver that causes each of the switch elements of the sensor to switch between a conductive state and non-conductive state so as to release charge from each of the semiconductor elements;

a reader that performs readout of a signal value according to an amount of the charge released from the each of the semiconductor elements; and a second hardware processor that receives input of an imaging condition that affects a dose of radiation reaching the sensor according to a user operation, wherein the first hardware processor:
sets the imaging condition received by the second hardware processor,
selects a gate readout pattern according to the set imaging condition set among different gate readout patterns; and
drives the readout unit using the selected gate readout pattern.

To achieve at least one of the abovementioned objects, a recording medium reflecting one aspect of the present invention is a non-transitory storage medium storing a computer-readable program for a radiographic imaging device, wherein the radiographic imaging device includes:

a first hardware processor;

a sensor that includes multiple semiconductor elements arranged two-dimensionally and multiple switch elements respectively connected to the semiconductor elements;

a gate driver that causes each of the switch elements of the sensor to switch between a conductive state and non-conductive state so as to release charge from each of the semiconductor elements; and a reader that performs readout of a signal value according to an amount of the charge released by the each of the semiconductor elements of the sensor, wherein the program causes the first hardware processor of the radiographic imaging device to:
set an imaging condition that affects a dose of radiation reaching the sensor;
select a gate readout pattern according to the set imaging condition among different gate readout patterns; and
drive the gate driver and the reader using the selected gate readout pattern.

BRIEF DESCRIPTION OF THE DRAWINGS

The advantages and features provided by one or more embodiments of the invention will become more fully understood from the detailed description given hereinbelow and the appended drawings which are given by way of illustration only, and thus are not intended as a definition of the limits of the present invention, wherein:

FIG. 10A shows the first gate readout pattern.

FIG. 10B shows the second gate readout pattern.

DETAILED DESCRIPTION OF THE EMBODIMENTS

Hereinafter, embodiments of the present invention are described with reference to the drawings. However, the scope of the present invention is not limited to the embodiments and illustrated examples.

It is known that a bias voltage applied in a radiographic imaging device repeatedly varies from and returns to a reference value every time switching of various kinds is performed in the device.

The inventor of the present invention has found as a result of painstaking research that a bias voltage greatly fluctuates particularly in imaging where a radiation dose received by the device is large, namely that an amount of charge generated by semiconductor elements of the device is large (for example, lateral imaging of the lumbar spine), and that it takes time for a bias voltage to return to the reference value in such imaging.

The inventor has also found that voltages in switching are different depending on whether radiation is being emitted or not due to a difference in the time it takes to return to the reference value, and there arises a difference between offset components and offset images in a radiographic image, which causes an abnormality in the image quality.

The present invention is intended to decrease influences of fluctuations in the bias voltage even in imaging under imaging conditions which may increase the dose of radiation reaching the radiographic imaging device and not to cause an abnormality in the image quality in a generated radiographic image.

1. Radiographic Imaging System

First, a radiographic imaging system according to this embodiment (hereinafter referred to as a system 100) is described.

Figure 1:
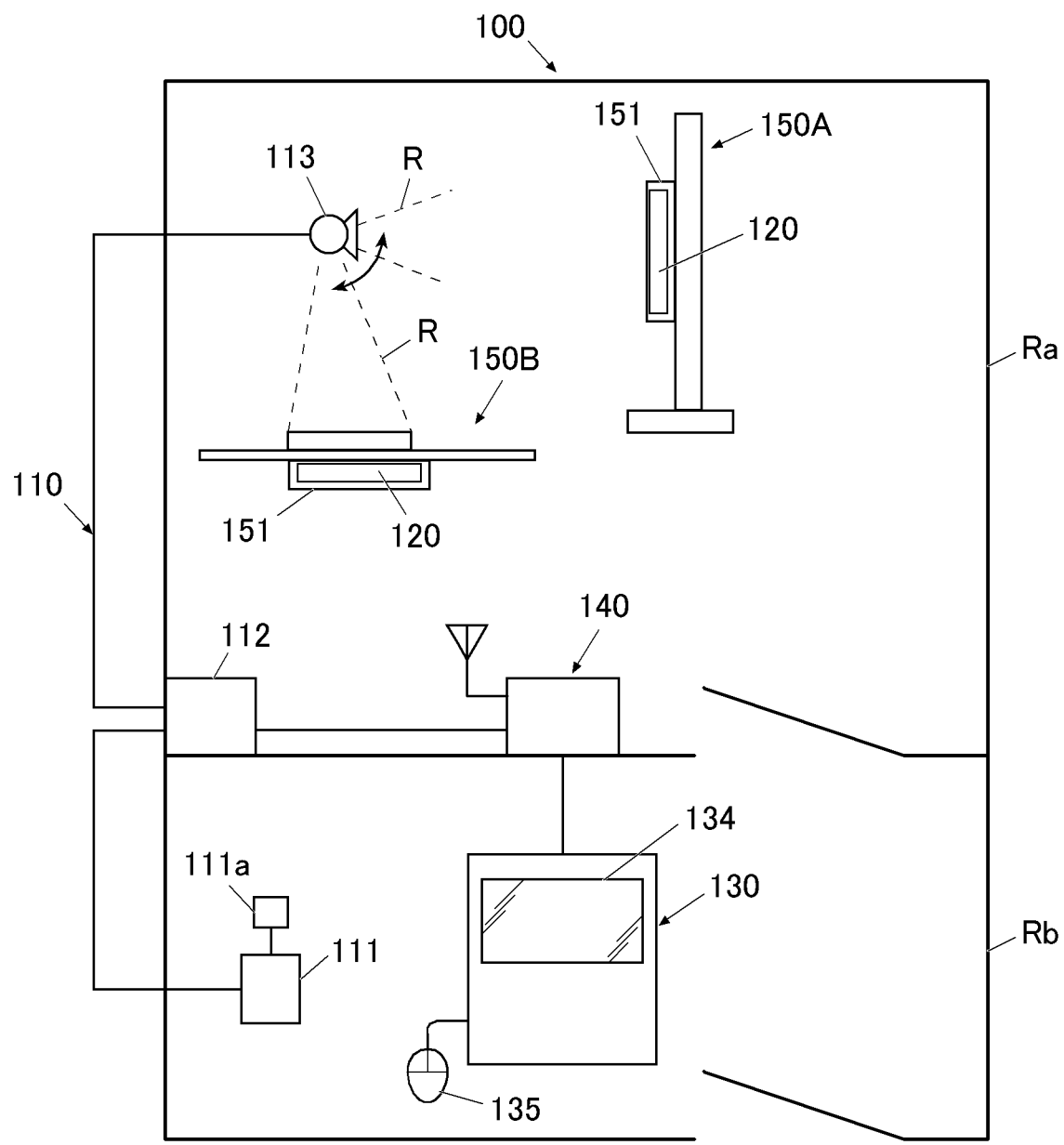
FIG. 1 is a block diagram showing a radiographic imaging system according to an embodiment of the present invention.

FIG. 1 is a block diagram showing the system 100.

The system 100 includes a radiation generating device 110, a radiographic imaging device (imaging device 120), a console 130, and a relay 140.

The devices 110 to 140 are communicable with each other via a network N (LAN (local area network), WAN (wide area network), Internet, etc.), for example.

The system 100 according to this embodiment includes imaging boards 150A and 150B.

The system 100 may be communicable with a hospital information system (HIS), a radiology information system (RIS), a picture archiving and communication system (PACS), and the like not shown in the drawings.

Radiation Generating Device

The radiation generating device 110 includes an operation table 111, a generator 112, and a radiation source 113.

The operation table 111 includes an emission command switch 111a that is operable by a user such as a radiologist. The operation table 111 commands a start of radiation emission to the generator 112 based on operation of the emission command switch 111a.

In response to the operation of the emission command switch 111a, the generator 112 applies a voltage according to predetermined imaging conditions (described later in detail) to the radiation source 113 (tube).

When a voltage is applied by the generator 112, the radiation source 113 generates radiation R (X-ray, for example) at a dose corresponding to the applied voltage.

The radiation source 113 can be moved in the X-axis direction and the Y-axis direction orthogonal to the X axis, and can be rotated around the rotation axes respectively parallel to the Y and Z axes so as to change the direction of the irradiation port.

The radiation generating device 110 generates radiation R according to the imaging mode (static imaging, dynamic imaging).

In static imaging, radiation R is emitted just one time for a single imaging action (press of the radiation command switch 111a).

In dynamic imaging, pulsed radiation R is emitted multiple times per specific time (15 times per second, for example) for a single imaging action, or radiation R is continuously emitted for a predetermined period of time.

Radiographic Imaging Device

The imaging device 120 generates a radiographic image according to the dose of the emitted radiation R in synchronization with the timing at which the radiation R is emitted by the radiation generating device 110.

In static imaging, a radiographic image is generated just one time for a single imaging action.

In dynamic imaging, a frame of a movie are repeatedly generated multiple times for a single imaging action per specified time (15 times per second, for example).

The imaging device 120 is described later in detail.

Console

The console 130 receives input of imaging conditions set on at least one of the radiation generating device 110 and the imaging device 120.

The console 130 includes a personal computer and a dedicated device.

The console 130 according to this embodiment may receive input of imaging conditions by the user operation (for example, of a technician) or based on the imaging order information acquired from other systems (HIS, RIS, etc.).

The console 130 is described later in detail.

Relay

The relay 140 functions as an access point or a hub for relaying wired or wireless communication between the devices 110 to 130.

Alternatively, the devices 110 to 130 may communicate with each other without the relay 140 in between.

In the system 100 as described above, in response to a user operation of the emission command switch 111a, the radiation generating device 110 emits radiation R to the subject under predetermined conditions.

Then, the imaging device 120 positioned behind the subject receives the radiation R transmitted through the subject, reads out image data based on it, and sends the image data to the console 130 via the relay 140.

The system 100 may be located inside a building as shown in FIG. 1, for example, or may be used as a mobile medical vehicle not shown in the drawings.

In the case where the radiographic imaging system 100 is located inside a building, the radiation source 113 of the radiation emitting device 10, the generator 112, the imaging device 120, the relay 140, and the like are installed in an imaging room Ra, and the operation table 111, the console 130, and the like of the radiation generating device 110 are installed in a front room Rb. The imaging device 120 may be installed in a cassette holder 151 of the imaging board (the imaging board 150A for standing position imaging and the imaging board 150B for lying position imaging). The relay 140 installed inside the imaging room Ra may maintain wireless communication or facilitate wired connection even when the console 130 is installed in the front room Rb.

In the case where the system 100 is used for a mobile medical vehicle, the components except the imaging device 120 are installed inside the mobile medical vehicle and the imaging device 120 can be carried around. In radiographic imaging in the mobile medical vehicle, the imaging device 120 is inserted between the bed and the patient lying on the bed or put on the patient. The imaging device 120 and the console 130 may communicate with each other using direct communication without the relay 140, or via the relay 140 not shown in the drawings.

2. Details of Console

Next, the above-mentioned console 130 included in the system 100 is described in detail.

Figure 2:
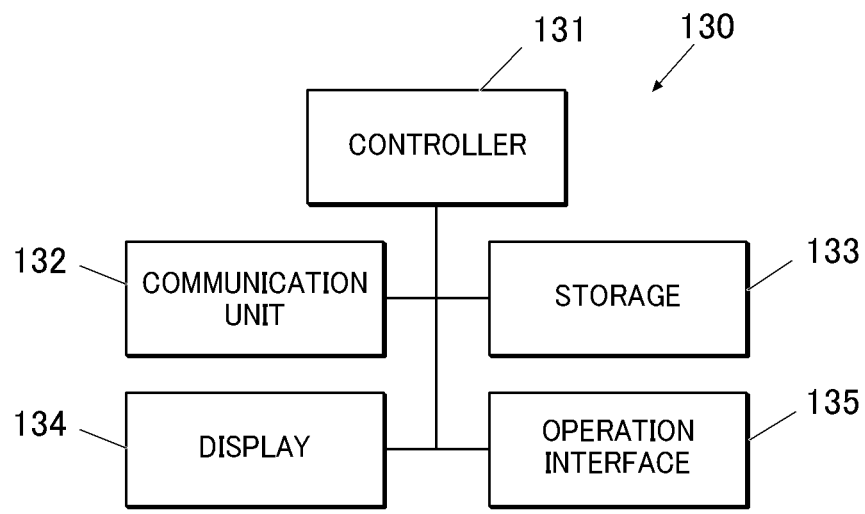
FIG. 2 is a block diagram showing a console included in the radiographic imaging system in FIG. 1.
Figure 3:
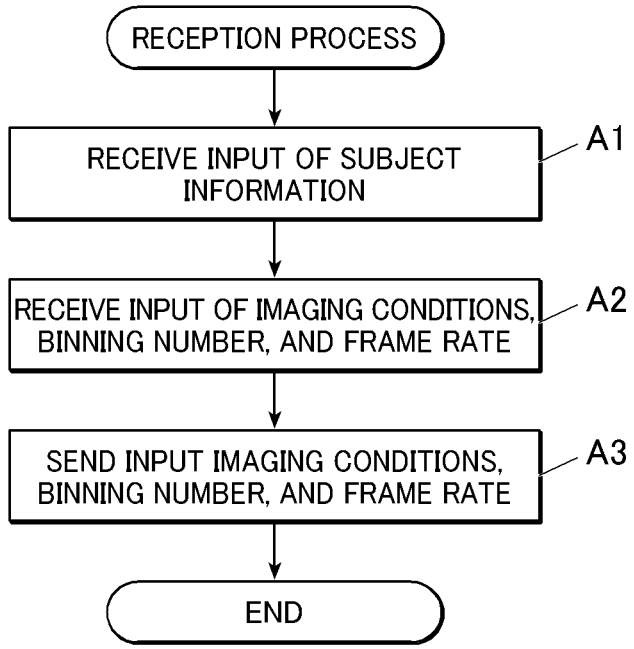
FIG. 3 is a flowchart showing a reception process executed by the console of FIG. 2.
Figure 4:
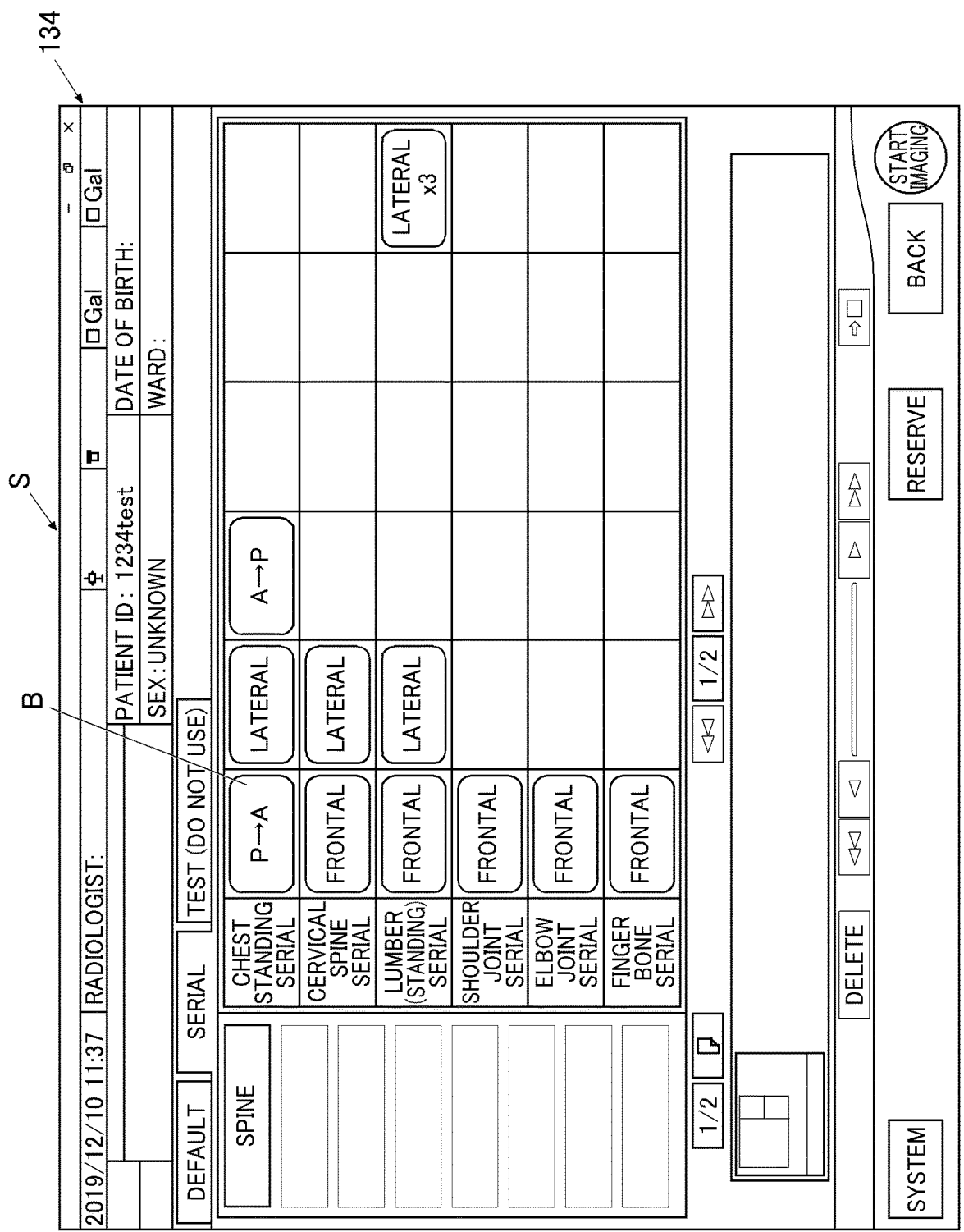
FIG. 4 shows an example of a screen displayed by the console of FIG. 2.
Figures 5, 6:
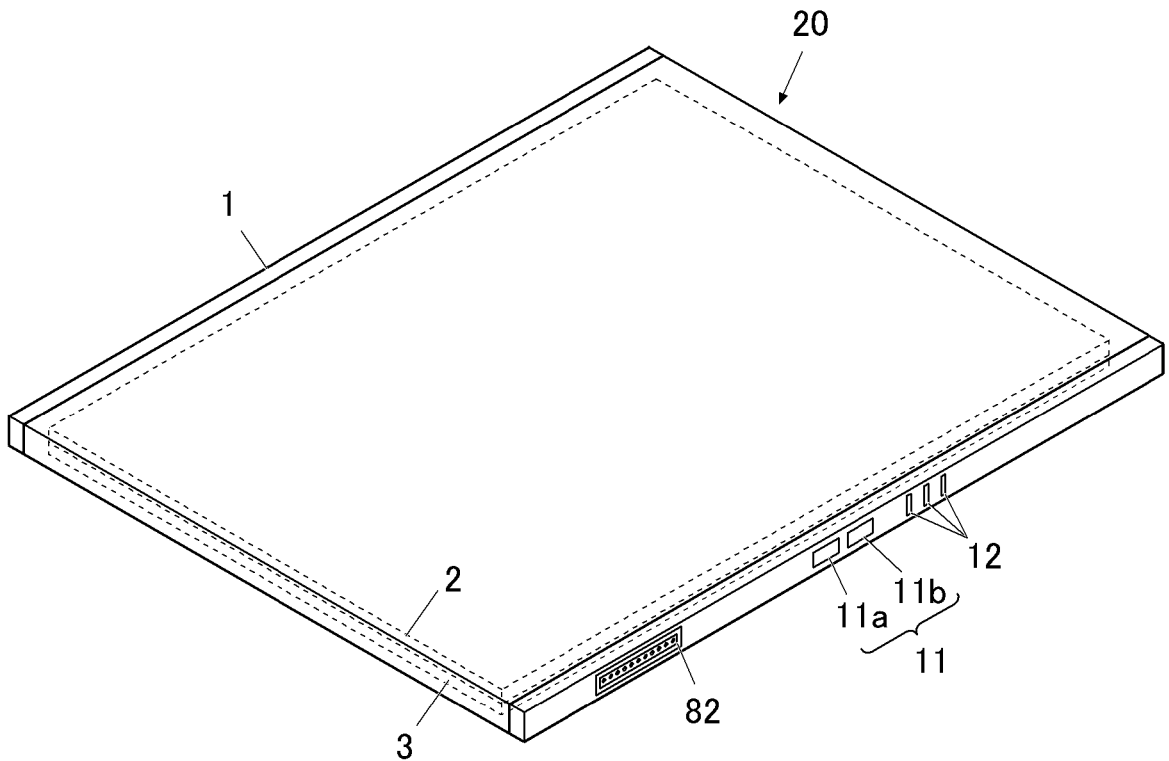
FIG. 5 shows relations of imaging conditions and a binning number, a framerate, and a gate period.
FIG. 6 shows a perspective view of a radiographic imaging device of the radiation imaging system in FIG. 1.

FIG. 2 is a block diagram showing the console 130. FIG. 3 is a flowchart showing a reception process executed by the console 130. FIG. 4 shows an exemplary screen displayed by the console 130. FIG. 5 shows relations of the imaging conditions and the binning number, the framerate, and the gate period.

Configuration of Console

The console 130 includes a controller 131 (second hardware processor), a communication unit 132, a storage 133, a display 134, and an operation interface 135, as shown in FIG. 2.

The components 131 to 135 are electrically connected with each other by a bus or the like.

The controller 131 includes a central processing unit (CPU) and a random access memory (RAM).

The CPU of the controller 131 reads out system programs and various types of processing programs stored in the storage 133, deploys them to the RAM, and centrally controls the operations of the components in the console 130 in accordance with the deployed programs.

The communication unit 132 includes a communication module.

The communication unit 132 sends and receives various signals and data with other devices connected by wire or wirelessly via a communication network N (local area network (LAN), wide area network (WAN), or the like).

The storage 33 includes a non-volatile semiconductor memory and a hard disk.

The storage 33 stores various programs executed by the controller 131 and parameters necessary for execution of the programs.

The storage 133 according to this embodiment may store image data of radiographic images.

The display 134 displays various screens.

The display 134 includes a liquid crystal display (LCD), an electronic luminescent display (ELD), and a cathode ray tube (CRYT).

The display 134 displays a list, radiographic images, and the like according to image signals received from the controller 131.

The operation interface 135 is an operating means that is operable by users.

The operation interface 135 according to this embodiment includes a keyboard having cursor keys, numeric keys, and various function keys, a pointing device such (a mouse or the like), and a touch panel superimposed on the surface of the display 134.

The operation interface 135 outputs control signals according to the operation by users to the controller 131.

Actions of Console

The controller 131 of the console 130 configured as described above executes a reception operation as shown in FIG. 3, for example, triggered by establishment of a predetermined condition.

A predetermined condition includes, for example, turning on the power, starting an application, and receiving a predetermined control signal from a device.

In this reception process, the controller 131 first executes a subject information reception process (Step A1).

The controller 131 receives input of subject information (name, subject ID, date of birth, sex, etc.) in the subject information reception process.

After receiving the subject information, the controller 131 executes an imaging condition reception process (Step A2).

The controller 131 receives input of imaging conditions according to the user operation via the operation interface 135 in the imaging condition reception process.

The imaging conditions include at least one of an imaged site (chest, lumbar spine, etc.), positioning (PA, LAT, etc.), a tube voltage, a tube current, an irradiation time, a milliampere-second value, an SID, presence/absence of grids, presence/absence of an additional filter, type of an additional filter (material (Al, Cu, etc.), thickness, etc.) which affects the dose of radiation to reach the sensor.

The controller 131 displays a setting screen S as shown in FIG. 4, for example, on the display 134 in the imaging condition reception process.

A button B for positioning selection is displayed for each imaged site on the setting screen S according to this embodiment. The controller 131 receives selection (input) of imaging conditions (imaged site and positioning) according to the operation (click or touch of a desired selection button B) performed by the user on the operation interface 135.

In the imaging condition reception process according to this embodiment, the controller 131 receives input of a binning number according to the user operation via the operation interface 135.

The console 130 according to this embodiment stores default values for the binning number associated with the selection buttons B, and in response to operation of a selection button B, the console 130 receives input of the binning number associated with the concerning selection button B.

The button B for positioning selection may be subdivided according to the binning number.

The binning number may be input separately.

In the imaging condition reception process according to this embodiment, the controller 131 receives input of a framerate according to the user operation via the operation interface 135.

In the imaging condition reception process according to this embodiment, the controller 131 displays a settable range of the framerate received from the imaging device 120, and the user can input (select) the framerate within that range.

The settable range includes comparatively high values for sites which can be imaged at a low dose (for example, chest), and includes comparatively low values for sites Y which need to be imaged at a high dose.

The settable rage may include higher values for readout with a larger binning number (ex. 2), and lower values for readout with a smaller binning number (ex. 1). This is because the time taken for one-time scanning increases as the binning number is smaller.

A default value of the framerate according to the combination of the imaging condition and the binning number may be associated with the button B for positioning selection, where the controller 131 receives input of the framerate that is associated with the operated selection button B.

The default value of the framerate may be the maximum settable value, or an adjusted value in consideration of a balance with the exposure dose. This saves users the burden to select the framerate every time.

In the imaging condition reception process according to this embodiment, the controller 131 may receive input of imaging conditions besides the imaged site and the positioning on a setting screen not shown in the drawings.

The binning number and the framerate determined based on the imaged site and the positioning may be adjusted based on a height, weight, sex, BMI, body thickness, age, or the like.

The controller 131 executes the reception process described above as a receiving means.

After having received input of the binning number and the framerate, the controller 131 sends the input imaging conditions, the binning number, and the framerate to the imaging device 120, as shown in FIG. 3 (Step A3).

3. Details of Radiographic Imaging Device

Next, the above-mentioned imaging device 120 in the system 100 is described in detail.

Figure 7:
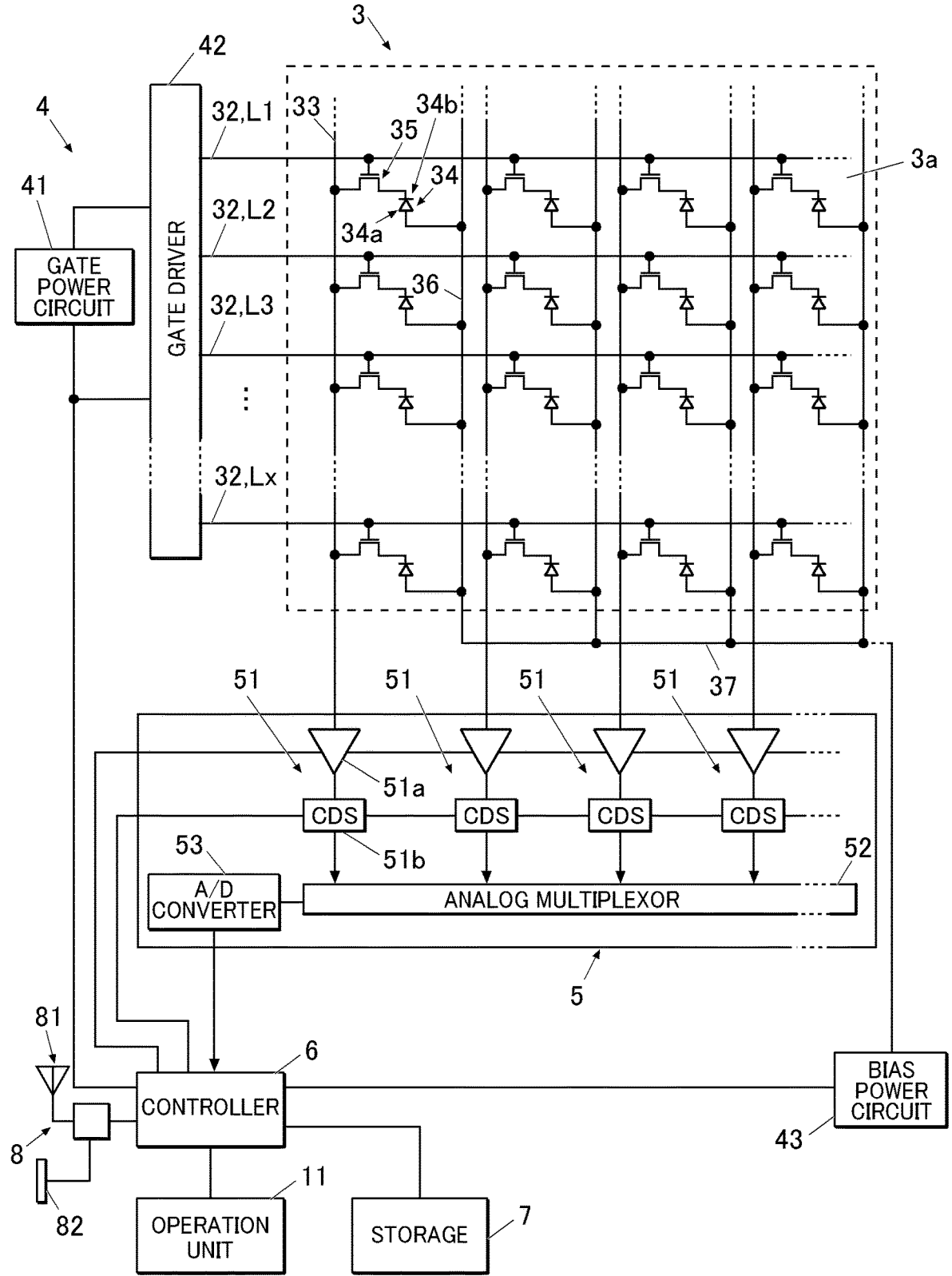
FIG. 7 is a block diagram showing an electrical configuration of the radiographic imaging device in FIG. 6.

FIG. 6 shows a perspective view of the imaging device 120, and FIG. 7 is a block diagram showing an electrical configuration of the imaging device 120.

The imaging device 120 according to this embodiment includes a case 1, and further includes a scintillator 2, a sensor 3, a gate drive unit 4, a reader 5, a controller 6 (hardware processor), a storage 7, and a communication unit 8 inside the case 1.

The components 3 to 8 receive power from a built-in or an external power supply not shown in the drawings.

The imaging device 120 may be of a portable type that can be carried around, or a fixed type that is installed in a room or on an imaging board.

1-1. Case

The case 1 according to this embodiment is formed in a panel shape as shown in FIG. 6.

The case 1 includes an operation interface 11 and an indicator 12 on one lateral surface.

The operation interface 11 includes a power switch 11a and various operation switches 11b, and can be operated by users.

1-2. Scintillator

The scintillator 2 is formed in a plate shape with a material (for example, columnar crystals of cesium iodide) that emits, when irradiated, electromagnetic waves having a longer wavelength than visible light in a dose of the irradiation.

There may be a reflective layer on a surface facing the sensor 3 in the scintillator 2 so that a larger amount of electromagnetic waves are transmitted by the sensor 3.

1-3. Sensor

The sensor 3 includes a substrate 31, scanning lines 32, signal lines 33, semiconductor elements 34, switch elements 35, bias lines 36, a connection line 37, as shown in FIG. 7.

The base board 31 is formed in a plate shape, and is arranged to face the scintillator 2 in parallel.

The scanning lines 32 according to this embodiment are arranged on the surface of the base board 31 to extend parallel to one another at predetermined intervals.

The signal lines 33 extend parallel to one another at predetermined intervals and orthogonal to the scanning lines 32, and are arranged so as not to electrically conductive to the scanning lines at the crossing parts.

That is, the scanning lines 32 and the signal lines according to this embodiment are arranged to be gridded.

The semiconductor elements 34 are two-dimensionally arranged on the surface of the base board 32, and are facing the scintillator.

The semiconductor elements 34 are provided in sections 3a defined by the grids of the scan lines 32 and the signal lines 33, thereby being arranged in a matrix.

The sections 3a correspond to pixels of a radiographic image.

Each of the semiconductor elements 34 is a photodiode, a phototransistor, or the like, and generates charge in an amount corresponding to the amount of the electromagnetic waves generated by the scintillator 2 (the dose of the radiation received by the imaging device 120).

A terminal 34a of the semiconductor element 34 is connected to a drain of a switch element 35, and the other terminal 34b is connected to a bias line 36.

Here, the semiconductor element 34 generates charge in an amount corresponding to the amount of the electromagnetic waves (light) generated by the scintillator 2, but the semiconductor element 34 may directly convert radiation into charge.

In the case where the semiconductor element 34 directly converts radiation into charge, the scintillator 2 may be omitted.

The switch elements 35 according to this embodiment are provided in the sections 3a defined by the grids of the scan lines 32 and the signal lines 33, similarly to the semiconductor element 34.

The switch elements 35 are thin film transistors (TFT), where a gate electrode is connected to the scanning line 32 nearby, a source electrode is connected to the signal line 33 nearby, and a drain electrode is connected to a terminal of the semiconductor element 34 in the same section.

Each of the switch elements 35 can switch the conducting state and the non-conducting state of the semiconductor element 34 and the signal line 33 (charge amplifier 51a) according to a voltage applied to the gate electrode (ON voltage $V_{ON}$/OFF voltage $V_{OFF}$).

The bias lines 36 are each connected to the other terminal 34b of the semiconductor element 34.

The bias lines 36 according to this embodiment are connected via the connection line 37, but may be directly connected to the bias power supply circuit 43, or alternatively, the bias lines 36 may be separately connected to multiple connection lines 37. As the bias lines 36 are connected with one connection line 37, a current in the bias lines 36 concentrates and a voltage drop due to wiring resistance may get large. As the bias lines 36 are connected with multiple connection lines 37, the current is divided and the voltage drop may be suppressed.

The bias lines 36 may extend in a planar shape, or in a grid shape where vertical and horizontal lines are connected at crossing points.

In the case where the bias lines are in a planar or grid shape, the connection line 37 may be omitted.

1-4. Gate Drive Unit

The gate drive unit 4 includes a gate power supply circuit 41, a gate drive driver 42 and a bias power supply circuit 43.

The gate power supply circuit 41 generates different voltages, an ON voltage $V_{ON}$ and an OFF voltage $V_{OFF}$, and supplies a voltage to the gate driver 42.

The gate driver 42 can switch between the scanning lines 32, choosing which of them an ON voltage $V_{ON}$ is applied to.

The OFF voltage $V_{OFF}$ is applied to the scanning lines 32 to which the ON voltage $V_{ON}$ is not applied.

The bias power supply circuit 43 generates a bias voltage Vb and applies the bias voltage Vb to each of the semiconductor elements 34 via the connection line 37 and the bias lines 36.

The gate drive unit 4 emits charge from each of the semiconductor elements by switching between the conducting state and the non-conducting state of the switch element 35 of the sensor 3.

1-5. Reader

The reader 5 includes a plurality of readout circuits 51, an analog multiplexor 52, and an A/D convertor 53.

Though the analog multiplexor 52 and the A/D converter 53 are each uniquely provided in FIG. 7, multiple readers 5 may be provided respectively with readout circuits 51, analog multiplexors 52, and A/D converters 53.

The readout circuits 51 are connected to the signal lines 33 respectively corresponding to the rows of semiconductor elements 34.

Each of the readout circuits 51 includes a charge amplifier 51a, a correlated double sampling circuit (hereinafter referred to as a CDS circuit 51b).

The readout circuit 51 generates an analog signal VA based on an amount of charge input via the signal line 33, and outputs the signal to the analog multiplexor 52.

The readout circuit 51 is described later in detail.

Output terminals of the readout circuits 51 are connected to the analog multiplexor 52.

The analog multiplexor 52 selectively switches the readout circuits 51 to be connected to the A/D convertor 53, thereby allowing analog signal values VA input from the readout circuits 51 to be output to the A/D convertor 53 one by one.

The A/D convertor 53 successively converts the input analog signal values VA into digital signal values V.

Though the A/D converter 53 is uniquely provided for multiple CDS circuits 51b, multiple A/D converters 53 may be respectively provided for the CDS circuits 51b.

In that case, the analog multiplexor 52 may be omitted.

The reader 5 as configured above reads out signal values V according to the amount of electric charge emitted by each of the semiconductor elements 34 of the sensor 3.

1-6. Controller

The controller 6 includes a central processing unit (CPU), a random access memory (RAM), and a read only memory (ROM).

The CPU of the controller 6 reads out system programs and various types of processing programs stored in the ROM, deploys them to the RAM, and centrally controls the operations of the components in the imaging device 120 in accordance with the deployed programs.

The ROM stores multiple gate reading out patterns, multiple sets of correction data (described later in detail), and the like.

The controller 6 generates image data of radiographic images according to signal values V read out by the reader 5.

The controller 6 may be composed of a complex programmable logic device (CPLD), a field programmable gate array (FPGA), or the like.

1-7. Storage

The storage 7 according to this embodiment is composed of a volatile memory (for example, a dynamic random access memory (DRAM)).

The storage 7 can store the image data of radiographic images generated by the controller 6.

Alternatively, the storage 7 may be composed of a non-volatile memory (for example, a flash memory).

The storage 7 may store multiple gate reading out patterns, sets of correction data, and the like, instead of the ROM in the controller 6.

1-8. Communication Unit

The communication unit 8 includes a communication module, for example, and is capable of wired or wireless communication with other devices (the console, the radiation generating device, and the like) via the antenna 81 and the connector 82

The connector 82 is exposed on one lateral surface of the case 1, as shown in FIG. 6.

4. Detailed Configuration of Readout Circuit

Next, a detailed configuration of the readout circuit 51 in the reader 5 of the above-described imaging device 120 is described in detail.

Figure 8:
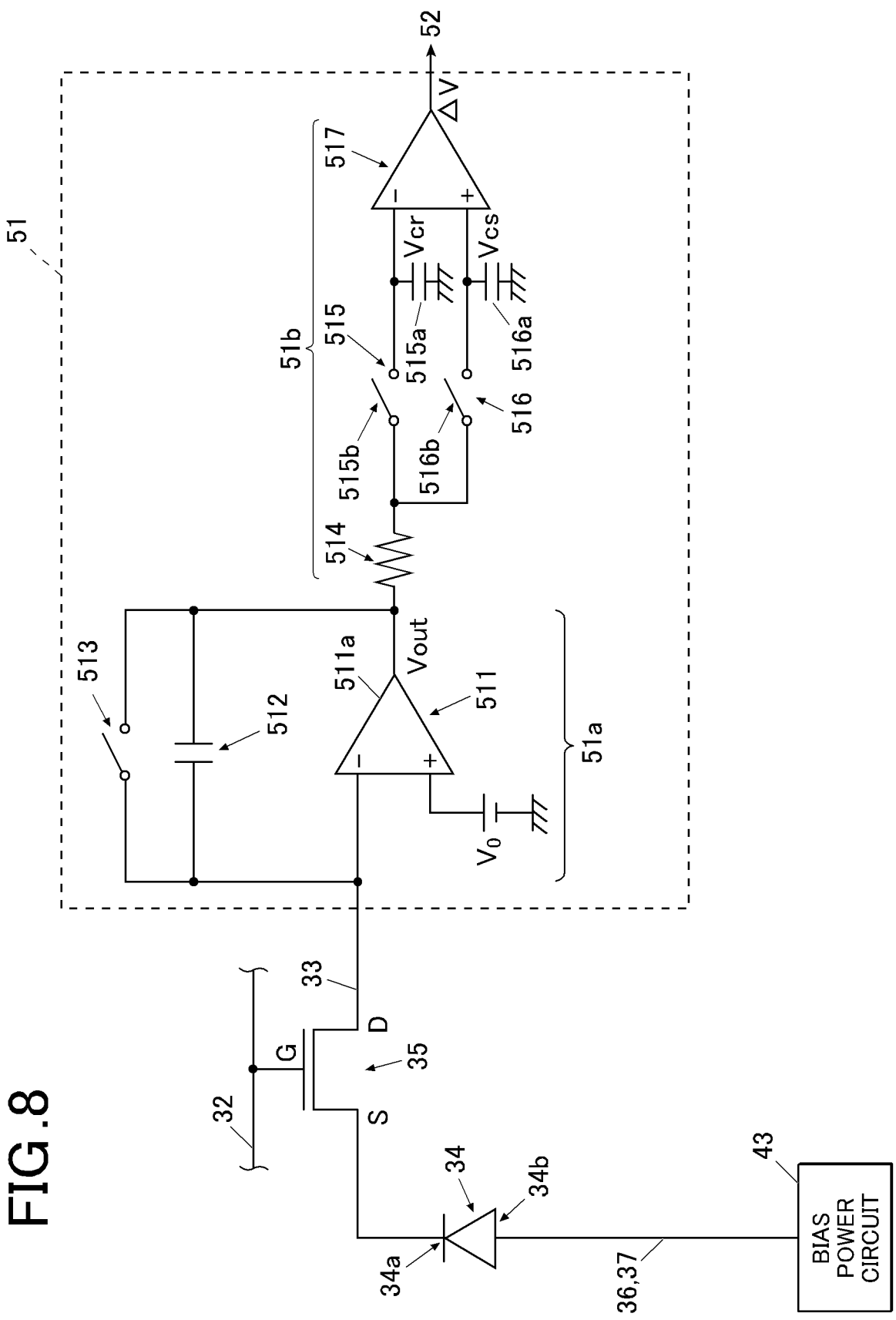
FIG. 8 shows a readout circuit of the radiographic imaging device in FIG. 6.

FIG. 8 is a circuit diagram showing a detailed configuration of the readout circuit 51.

Each of the readout circuits 51 includes a charge amplifier 51a and a CDS circuit 51b, as shown in FIG. 8, for example.

2-1. Charge Amplifier

The charge amplifier 51a incudes an operational amplifier 511, a capacitor 512, and a reset switch 513.

An inverting input terminal of the operational amplifier 511 is connected with the signal line 33, and a reference voltage V0 is applied to a non-inverting input terminal.

A ground potential may be applied as the reference voltage V0.

When charge flows via the signal line 33, an output voltage $V_{OUT}$ is output according to the amount of the charge.

The capacitor 512 and the reset switch 513 are connected in parallel between the inverting input terminal and the output terminal of the operational amplifier 511.

The charge amplifier 51a configured as described above can convert the amount of the charge emitted from the semiconductor element 34 into a voltage $V_{OUT}$ and output the voltage.

When the reset switch 513 is put into the conductive state, the charge in the capacitor 512 is released and is reset thereby.

2-2. CDS Circuit

The CDS circuit 51b includes a resistor 514, a first sample-and-hold circuit (hereinafter referred to as a CDS1 circuit 515), a second sample-and-hold circuit (hereinafter referred to as a CDS2 circuit 516), and a difference circuit 517.

The resistor 514 is connected with the output terminal of the operational amplifier 511 of the charge amplifier 51a in series.

The CDS1 circuit 515 includes a first capacitor 515a and a first switch 515b.

One electrode of the first capacitor 515a is connected between the resistor 514 and the inverting input terminal, and the other electrode of the first capacitor 515a is connected to the ground.

The first switch 515b is provided between the resistor 514 and the first capacitor 515a.

When the first switch 515b is put into the conductive state, the charge amplifier 51a and the first capacitor 515a are connected to each other, and the first capacitor 515a is charged.

Thereafter, when the first switch 515b is put into the non-conductive state, the charge amplifier 51a and the first capacitor 515a are disconnected from each other, ad a voltage between the electrodes of the first capacitor 515a (hereinafter referred to as a first voltage $V_{SHR}$) is held.

The CDS2 circuit 516 includes a second capacitor 516a and a second switch 516b.

One electrode of the second capacitor 516a is connected between the resistor 514 and of the non-inverting input terminal of the difference circuit 517, and the other electrode of the first capacitor 515a is connected to the ground.

The second switch 516b is provided between the resistor 514 and the second capacitor 516a.

When the second switch 516b is put into the conductive state, the charge amplifier 51a and the second capacitor 516a are connected to each other, and the second capacitor 516a is charged.

Thereafter, when the second switch 516b is put into the non-conductive state, the charge amplifier 51a and the second capacitor 516a are disconnected from each other, and a voltage between the electrodes of the second capacitor 516a (hereinafter referred to as a second voltage $V_{SHS}$) is held.

The inverting input terminal of the difference circuit 517 is connected to the CDS1 circuit 515, and the non-inverting input terminal to the CDS2 circuit 516.

The difference circuit 517 outputs to the analog multiplexor 52 a difference calculated by subtracting the first voltage $V_{SHR}$ in the CDS1 circuit 515 from the second voltage $V_{SHS}$ in the CDS2 circuit 516 as the above-mentioned analog signal value $V_A$.

5. Actions of Radiographic Imaging Device

Next, actions of the above-mentioned imaging device are described.

Figure 9:
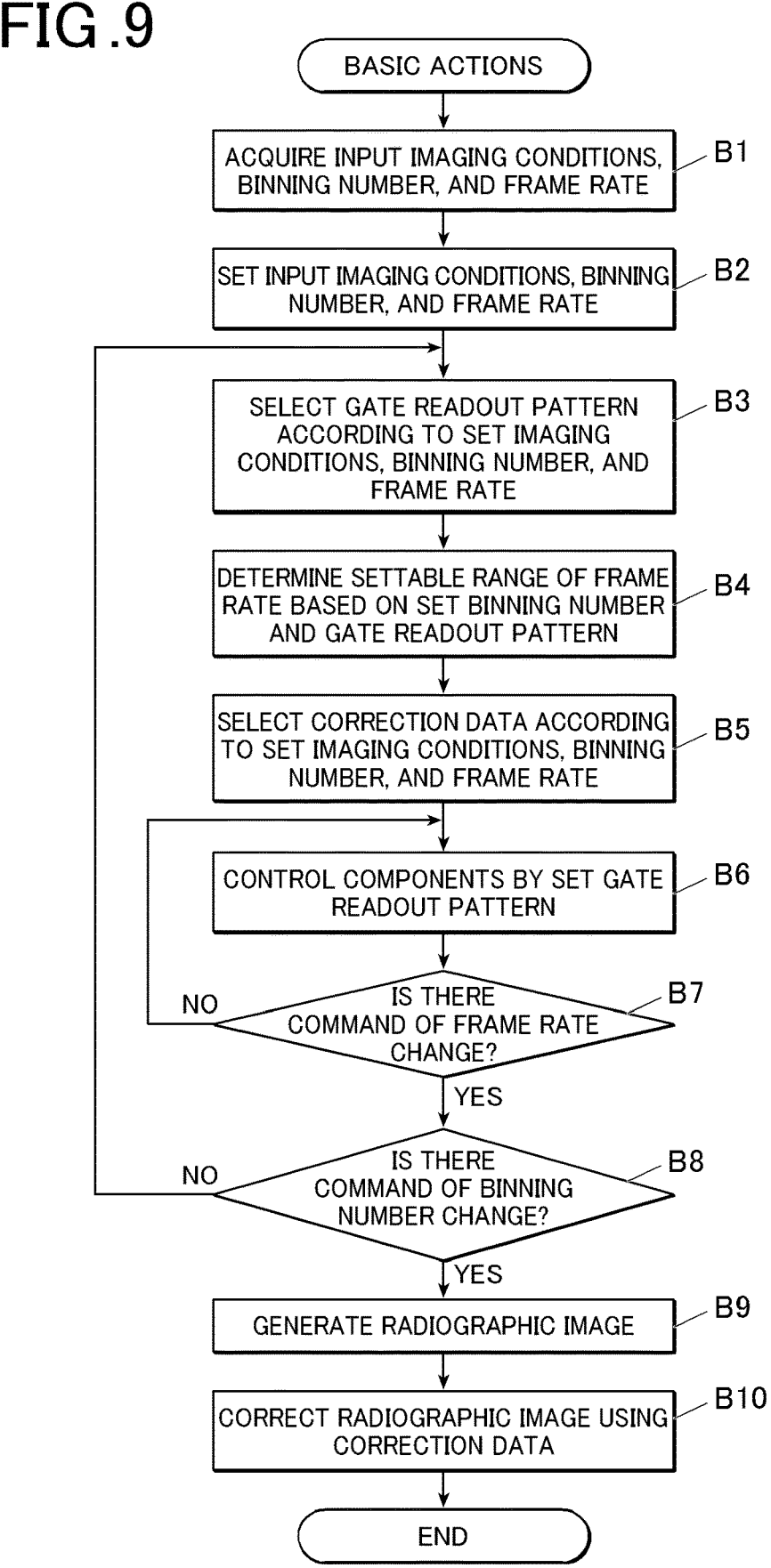
FIG. 9 is a flowchart showing a flow of basic actions performed by the radiographic imaging device in FIG. 6.
Figure 10A:
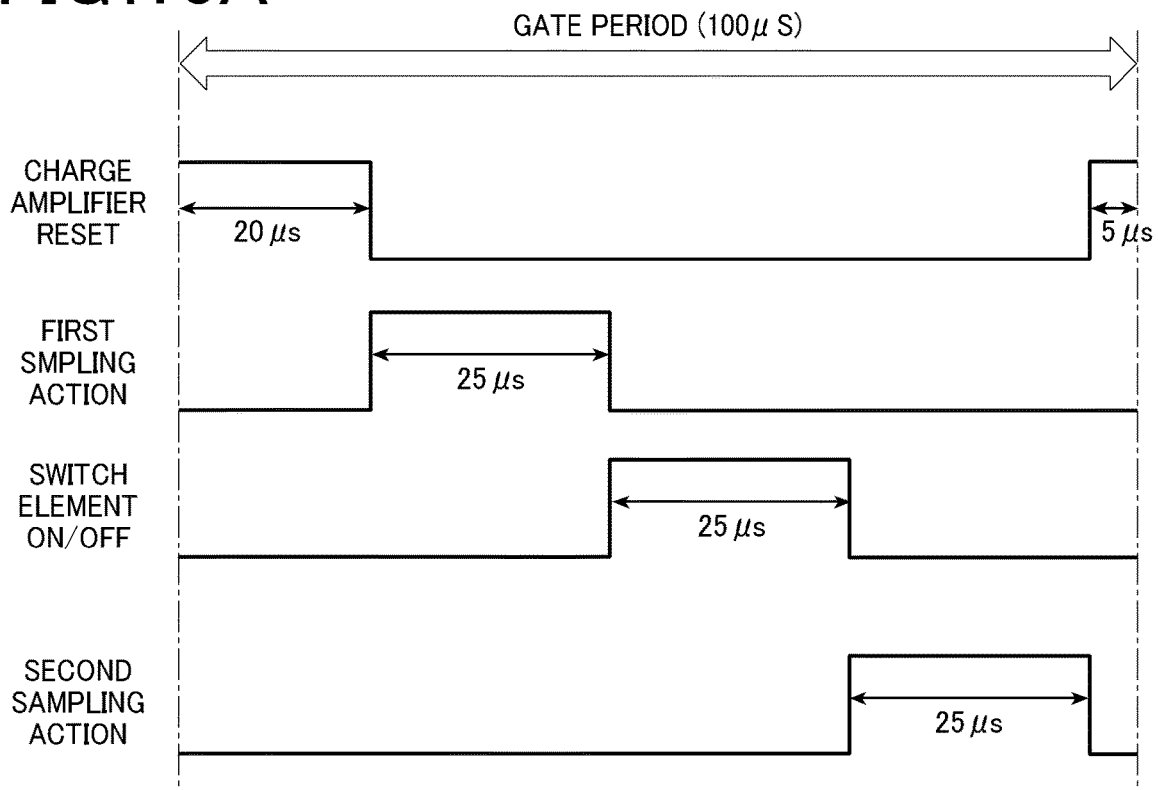
FIG. 10A is a timing chart showing an example of gate readout executed by the radiographic imaging device in FIG. 6.
Figure 10B:
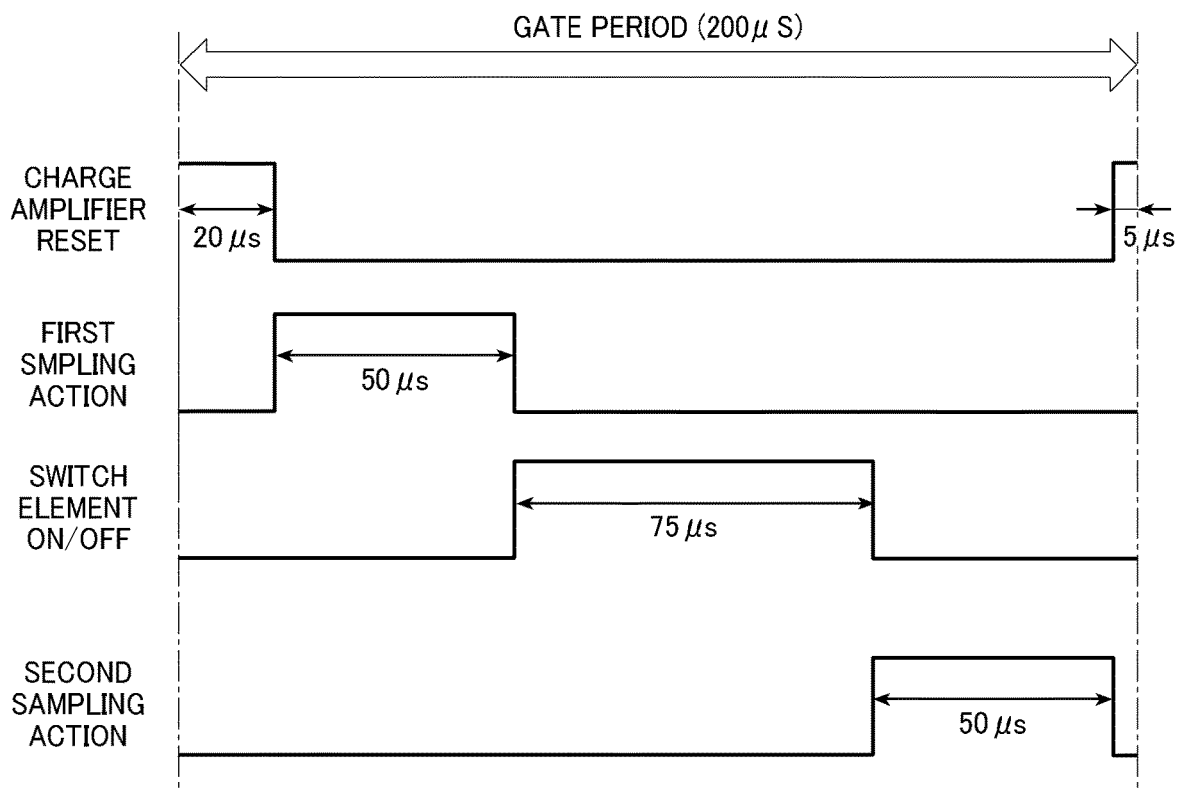
FIG. 10B is a timing chart showing an example of gate readout executed by the radiographic imaging device in FIG. 6.
Figure 11:
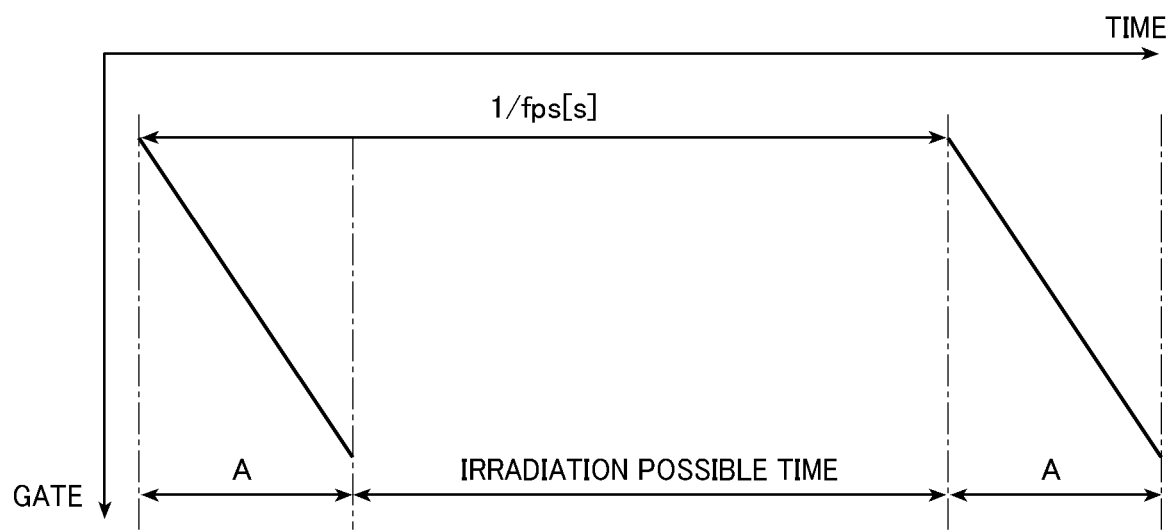
FIG. 11 shows relations of a period of a frame generation and a irradiation time.
Figure 12:
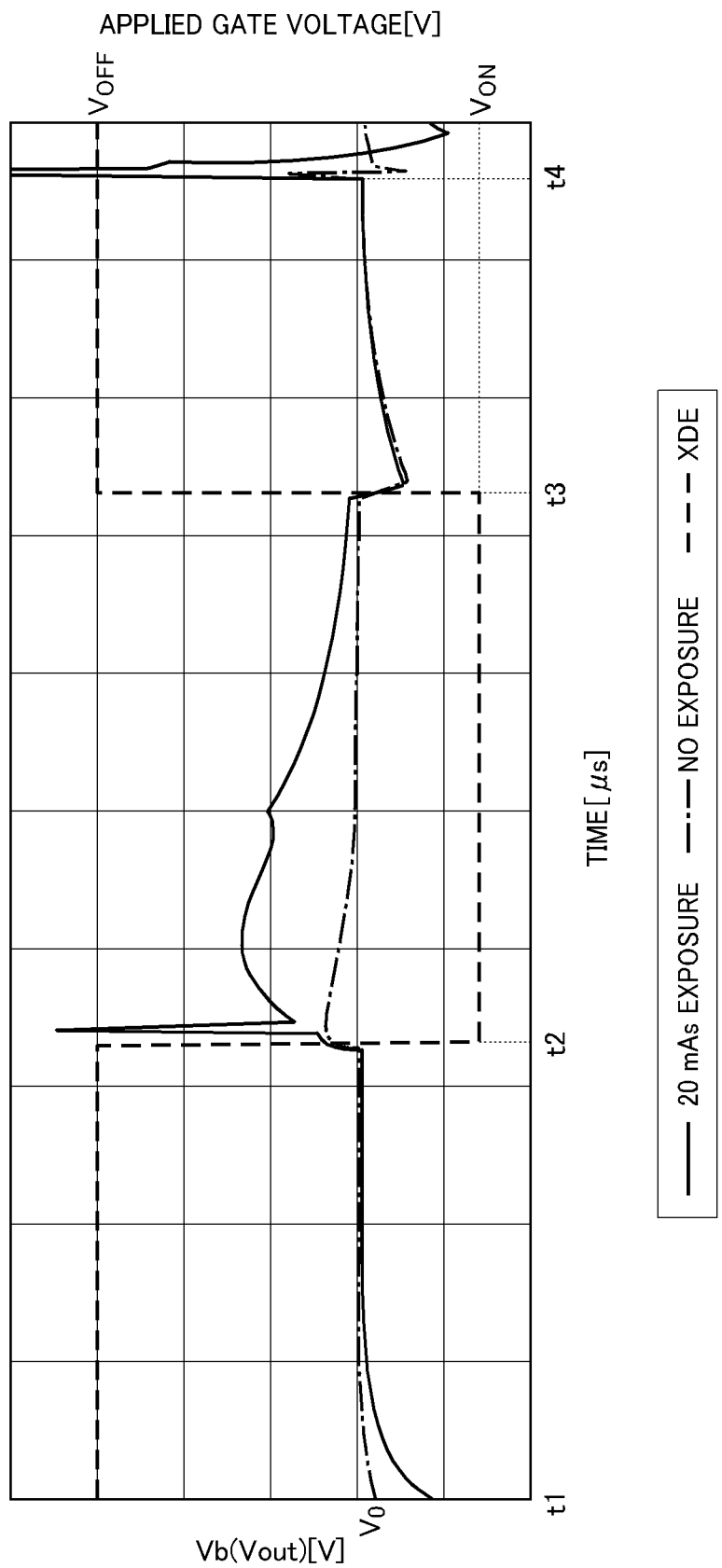
FIG. 12 shows a chronological change of actions of components of the radiographic imaging device and a bias voltage Vb (output voltage $V_{OUT}$ of a charge amplifier).

FIG. 9 is a flowchart showing a basic process executed by the imaging device 120. FIGS. 10A and 10B is a timing chart showing an example of a gate readout by the imaging device 120. FIG. 11 shows relations of frame generation periods and irradiation times. FIG. 12 is a graph showing a chronological change of the bias voltage Vb (output voltage $V_{OUT}$) in the gate readout.

When the power switch 11a of the imaging device 120 is turned on, the controller 6 starts basic actions as shown in FIG. 9, for example.

First, the controller 5 executes an acquisition process (Step B1) in this basic actions.

The controller 6 acquires imaging conditions from another device in this acquisition process.

In the acquisition process according to this embodiment, the console 130 acquires the imaging conditions received by the console 130.

The controller 6 may acquire the imaging conditions from the radiation generating device 110, the RIS, or the like in the acquisition process.

In the acquisition process according to this embodiment, the controller 6 acquires the binning number and the framerate from the console 130.

The controller 6 executes the acquisition process described above as an acquiring means.

After the imaging conditions are acquired, the controller 6 executes a setting process (Step B2).

The controller 6 sets the imaging conditions acquired at the above-described acquisition process in the setting process.

As described above, in the acquisition process according to this embodiment, the controller 6 acquires the imaging conditions from the console 130, and therefore the controller 6 sets the imaging conditions received by the console 130 in the setting process.

The controller 6 sets the binning number in the setting process according to this embodiment.

The controller 6 may set the imaging conditions, the binning number, and the framerate according to the operation via the operation interface 11 in the setting process.

In the setting process, an expected dose of radiation to reach the sensor 3 in the imaging may be calculated based on the set imaging conditions.

The controller 6 executes the above-described setting process as a setting means.

After having set the imaging conditions, the controller 6 executes a selection process (Step B3).

The controller 6 selects a gate readout pattern among multiple different gate readout patterns according to the imaging conditions.

The gate readout patterns are defined by at least one of the duration of the first sampling action, the duration of the second sampling action, and the duration of the conduction of the switch element, and the gate period by which the signal values V are read out.

The different gate readout patterns include the first gate readout pattern and the second gate readout pattern.

The first gate readout pattern is used for the imaging conditions with a low dose of radiation. As shown in FIG. 10A, the gate period and the durations of the first sampling action, the second sampling action, and the conduction of the switch element are comparatively short, for example.

In the second gate readout pattern, the gate period is longer than in the first gate readout pattern, as shown in FIG. 10B.

In the second gate readout pattern, at least one of the durations of the first sampling action, the second sampling action, and the conduction of the switch element is longer than in the first gate readout pattern (in FIG. 10B, all the durations are set to longer values).

In the case where the dose of radiation is calculated in the setting process, the controller 6 may select the gate readout pattern according to the arrival dose of radiation.

The controller 6 executes the above-described selection process as a selecting means.

After having selected the gate readout pattern, the controller 6 executes a determination process (Step B4), as shown in FIG. 9.

In the determination process, the controller 6 determines a settable range f the framerate based on the binning number set in the setting process and the gate readout pattern selected in the selection process.

In the determination process according to this embodiment, the controller 6 determines the range of the framerate based on the number of rows of the semiconductor elements 34 (the number of gate readouts to generate a radiographic image without binning), the gate period, and the binning number.

More specifically, the range of the framerate is calculated by Formula 1 shown below.

$$\text{Framerate} \leq 1/(\text{Number of Semiconductor Element Rows} \times \text{Gate Period} \div \text{Binning Number}) \quad (1)$$

After having calculated the range of the framerate, the controller 6 sends the calculated range to the console 130. This makes it possible to reset the framerate by the user.

During the time spent on generating a single frame, it is desirable that radiation is emitted within a irradiation possible time other than the time A for readout of signal values. There is a time necessary to generate a frame, an irradiation time T.

The controller 6 may determine the range of the framerate based on the irradiation time T in the determination process.

In that case, the controller 6 calculates an irradiation time T that can be kept in a single gate period based on the binning number and the framerate set in the setting process and the gate readout pattern selected in the selection process.

Specifically, the irradiation time T is calculated by Formulas 2 and 3 shown below.

$$A = \text{Number of Semiconductor Element Rows} \times \text{Gate Period} \div \text{Binning Number} \quad (2)$$

$$T = 1/\text{Framerate} - A \quad (3)$$

The range of the framerate is calculated by Formula (4) shown below.

$$\text{Framerate} \leq 1/(T + \text{Number of Semiconductor Element Rows} \times \text{Gate Period} \div \text{Binning Number}) \quad (4)$$

In a case where the user selects the imaging conditions (milliampere-second value/frame) and the irradiation time calculated based on the selected imaging conditions exceeds the irradiation possible time, the controller 6 may inhibit irradiation or output an alert.

Whether an alert is output or not may be simply determined based on whether Formula (5) shown below is satisfied or not, or may be determined based on whether Formula (6) shown below is satisfied or not in consideration of the effects of a waveform of radiation (for example, wave tail), the margin time necessary depending on the capacity of communication between devices, or the like.

$$\text{Irradiation Time } T > A \quad (5)$$

$$\text{Irradiation Time } T + \text{Margin Time} > A \quad (6)$$

The margin time may be switched according to the communication method (wired or wireless) or the radiation generating device 110 to be connected, or in consideration of both of them.

The controller 6 executes the above-described determination process as a determining means.

After having selected the gate readout pattern, the controller 6 executes a data selection process (Step B5).

In the data selection process, the controller 6 selects correction data according to at least one of the binning number, and the framerate set in the setting process, and the gate readout pattern selected in the selection process.

The correction data includes gain data and a defect map.

The gain data is information on the sensitivity of each of the conductor elements.

The defect map is information on the position(s) of a conductor element(s) that emits an abnormal amount of charge (signal value V read out by the reader 5).

Multiple sets of the correction data are different for each combination of different binning numbers, framerates, and gate readout patterns.

After having selected the gate readout pattern, the controller 6 executes a drive control process (Step B6).

In the drive control process, the controller 6 causes each of the readout circuits 51 to apply a reference voltage V0 to each of the signal lines 33, and causes the bias power supply circuit 43 to apply a bias voltage Vb to each of the conductor elements 34.

The controller 6 then drives the reader 5 by the gate readout pattern selected in the selection process.

Specifically, the controller 6 causes the gate drive unit 4 to apply an OFF voltage $V_{OFF}$ to all the scanning lines 32 to put all the switch elements 35 in the non-conductive state. Then, charges generated by the conductor elements are stored in each of the sections 3a.

After putting all the switch elements 35 in the non-conductive state, the controller 6 causes each of the charge amplifiers 51a to put the reset switch 513 in the conductive state to reset the charge amplifiers 51a.

After having reset the voltage of each of the charge amplifiers 51a, the controller 6 performs the first sampling action.

Specifically, the controller 6 put the first switch 515b in the conductive state, and charges power to the first capacitor 515a for a predetermined time (t1 to t2).

In this embodiment, as the multiple charge amplifiers 51a output a voltage to the multiple CDS1 circuits 515 respectively, the controller 6 causes the multiple CDS1 circuits 515 to perform the first sampling action at the same time.

The voltage between the electrodes of the first capacitor 515a after being charged for a predetermined time (the output voltage of the charge amplifier 51a after the switch element 35 is put in the non-conductive state) is held as the first voltage $V_{SHR}$ (t2).

The first voltage $V_{SHR}$ corresponds to the magnitude of a noise generated in readout.

Thereafter, the controller 6 causes the gate drive unit 4 to apply an ON voltage $V_{ON}$ to one of the scanning lines 32 so as to put each of the switch element elements 35 connected to that one of the scanning lines 32 in the conductive state. Then, a difference between the reference voltage V0 applied to the signal line 33 and the bias voltage Vb applied to the bias line 36 causes charges stored in each of the sections 3a connected to the scanning line 32 to which the ON voltage $V_{ON}$ is applied to be a current and flows to each of the signal lines 33. This way, the charges of the conductor elements 34 in the same row are reset (t2).

When the current flows to each of the signal lines 33, the charge amplifier 51a of each of the readout circuits 51 outputs an output voltage $V_{OUT}$ according to the current flowing from the signal line 33 to the CDS circuit 51b.

Thereafter, the controller 6 causes the gate drive unit 4 to apply an OFF voltage $V_{OFF}$ to the scanning line 32 to which an ON voltage $V_{ON}$ is applied so as to put the switch elements 35 connected to that scanning line 32 in the non-conductive state (t3).

After having put the switch elements 35 in the non-conductive state, the controller 6 performs the second sampling action.

Specifically, the controller 6 put the second switch 516b in the conductive state, and charges power to the second capacitor 516a for a predetermined time (t3 to t4).

In this embodiment, as the multiple charge amplifiers 51a output a voltage to the multiple CDS2 circuits 516 respectively, the controller 6 causes the multiple CDS2 circuits 516 to perform the second sampling action at the same time.

The voltage between the electrodes of the second capacitor 516a after being charged for a predetermined time (the output voltage of the charge amplifier 51a after the switch element 35 is put in the conductive state) is held as the second voltage $V_{SHS}$ (t2).

The second voltage $V_{SHS}$ corresponds to a noise generated in readout and a magnitude of the signal value V.

When the second voltage $V_{SHS}$ is held in each of the CDS circuits 516, each of the difference circuits 517 outputs an difference between the second voltage $V_{SHS}$ and the first voltage $V_{SHR}$ to the analog multiplexor 52.

The analog multiplexor 52 sequentially outputs the input analog signal values $V_A$ to the A/D converter 53.

The A/D converter 53 sequentially converts the input analog signal values $V_A$ into digital signal values V and outputs the values V to the controller 6.

Right after the start of the above-described drive control process, there may be an effect left before the process is performed (for example, a dark charge stored before imaging, an afterimage of the previous imaging) Thus, the controller 6 may execute a process in which the drive control process is executed without image generation (reset) right after the start of the drive control process.

The controller 6 may notify the user that the radiation cannot be emitted during the reset.

The controller 6 may execute the reset according to at least one of a combination of the binning number, the framerate, and the gate readout pattern, whether to change the patterns at Steps B7 and B8 described later, and a time interval from the previous imaging.

After the drive control process is started and before irradiation is started, the controller 6 monitors whether a command to change the framerate (a newly set value) is received from the console 130, as shown in FIG. 9 (Step B7).

If there is received a command to change the framerate (Step B7; YES), the controller 6 newly sets the framerate and continues the drive control process.

On contrary, if there is no command to change the framerate (Step B7; NO), the controller 6 continues the drive control process using the initial framerate.

After the drive control process is started and before irradiation is started, the controller 6 monitors whether a command to change the binning number (a newly set value) is received from the console 130 (Step B8).

If there is received a command to change the binning number (Step B8; YES), the controller 6 newly sets the binning number and returns to Step B3 (reset the gate readout pattern).

On contrary, there is no command to change the binning number (Step B8; NO), the controller 6 continues the drive control process using the initial binning number.

The actions from application of the ON voltage $V_{ON}$ to a scanning line 32 described above to this step are repeated for different scanning lines 32 to read multiple signal values V for one frame.

After the signal values V for one frame are read, the controller 6 generates a radiographic image based on the multiple signal values V (Step B9).

In a case where radiation is emitted while all the switch elements 35 are in the non-conductive state, the controller 6 generates an offset image.

On contrary, in a case where radiation is emitted while all the switch elements 35 are in the non-conductive state, the controller 6 generates an exposure image.

As irradiation, readout of multiple signal values for one frame, and generation of an exposure image are repeated multiple times using a predetermined framerate, a radiographic dynamic image composed of multiple frames is generated.

In the case where the binning number is set to 2 or larger in the above-described setting process, the controller 6 performs binning in the drive control process.

In the case where the binning number is 2, the controller 6 causes the gate driver 42 of the gate drive unit 4 the ON voltage $V_{ON}$ to two scanning lines 32 next to each other or causes the analog multiplexor 52 of the reader 5 to output analog signal values VA of two rows next to each other together.

The controller 6 executes the drive control process described above as a drive control means.

After having generated an exposure image, the controller 6 executes a correction process (Step B10).

In the correction process, the controller 6 performs offset correction of the exposure image using an offset image.

Further, in the correction process, the controller 6 corrects the exposure image after the offset correction using correction data (gain data, defect map) selected in the data selection process.

The controller 6 executes the correction process as a correcting means.

6. Effects

The imaging device 120 and the system including the imaging device 120 according to this embodiment described hereinbefore select a gate readout pattern among different gate readout patterns according to the set imaging conditions (a dose of radiation to reach the sensor 3) (a pattern with a longer gate period for a higher dose) and drive the gate drive unit 4 and the readout unit 5 using the selected gate readout pattern.

This makes it possible to secure a sufficient time for convergence of the bias voltage Vb, and offset components of an exposure image are equal to an offset image even when the dose of radiation is large.

Thus, the imaging device 120 and the system can generate an exposure image without abnormalities in the image quality even under the imaging conditions which often caused abnormalities.

What is claimed is:

1. A radiographic imaging device comprising:
   a first hardware processor;
   a sensor that includes multiple semiconductor elements arranged two-dimensionally and multiple switch elements respectively connected to the semiconductor elements;
   a gate driver that causes each of the switch elements of the sensor to switch between a conductive state and non-conductive state so as to release charge from each of the semiconductor elements; and
   a reader that performs readout of a signal value according to an amount of the charge released by the each of the semiconductor elements of the sensor;
   wherein the first hardware processor:
      sets an imaging condition that affects a dose of radiation reaching the sensor;
      selects a gate readout pattern according to the set imaging condition among different gate readout patterns; and
      drives the gate driver and the reader using the selected gate readout pattern,
   wherein the reader performs a first sampling action to hold a first output voltage after the each of the switch elements is in the non-conductive state,
   wherein the reader performs a second sampling action to hold a second output voltage after the each of the switch elements is in the conductive state, and
   wherein the gate readout pattern is defined by:
      at least one of a duration of the first sampling action, a duration of the second sampling action, and a duration of the conductive state of the each of the switch elements; and
      a gate period for repeating the readout of the signal value.

2. The radiographic imaging device according to claim 1, wherein the reader comprises a charge amplifier that converts the amount of the charge released from the each of the semiconductor elements into a voltage, and the first output voltage and the second output voltage are output voltages of the charge amplifier.

3. The radiographic imaging device according to claim 1, wherein the first hardware processor drives the reader in obtaining an exposure image using the gate readout pattern which is used in obtaining an offset image.

4. The radiographic imaging device according to claim 1 further comprising:
   an operation interface operable by a user; and
   an input unit that obtains the imaging condition input via a device other than the radiographic imaging device,
   wherein the first hardware processor sets the imaging condition according to a user operation via the operation interface.

5. The radiographic imaging device according to claim 1, wherein the first hardware processor:
   obtains the imaging condition from a device other than the radiographic imaging device; and
   sets the obtained imaging condition.

6. The radiographic imaging device according to claim 1, wherein the imaging condition is at least one of a site to be imaged and a position of the imaging device relative to the site to the imaged.

7. The radiographic imaging device according to claim 2, wherein the first hardware processor is capable of performing binning using a binning number,
   wherein the first hardware processor sets the binning number, and determines a settable range of a frame rate based on the set binning number and the selected gate readout pattern.

8. The radiographic imaging device according to claim 7, wherein the multiple semiconductor elements are arranged in a matrix,
   wherein the hardware processor determines a range of the frame rate based on a number of rows of the semiconductor elements, the gate period, and the binning number.

9. The radiographic imaging device according to claim 7, wherein the first hardware processor:
   selects, among different sets of correction data, a set of correction data according to at least one of the binning number set by the first hardware processor, the frame rate set by the first hardware processor, and the gate readout pattern selected by the first hardware processor; and
   corrects the image using the selected set of correction data.

10. The radiographic imaging device according to claim 8, wherein the first hardware processor determines the range of the frame rate based on a duration of irradiation necessary to generate a frame.

11. The radiographic imaging device according to claim 4, wherein the hardware processor sets the binning number and the frame rate according to the user operation via the operation interface.

12. A radiographic imaging system comprising:
    a first hardware processor;
    a sensor that includes multiple semiconductor elements arranged two-dimensionally and multiple switch elements respectively connected to the semiconductor elements;
    a gate driver that causes each of the switch elements of the sensor to switch between a conductive state and non-conductive state so as to release charge from each of the semiconductor elements;
    a reader that performs readout of a signal value according to an amount of the charge released from the each of the semiconductor elements; and a second hardware processor that receives input of an imaging condition that affects a dose of radiation reaching the sensor according to a user operation, wherein the first hardware processor:
  sets the imaging condition received by the second hardware processor,
  selects a gate readout pattern according to the set imaging condition set among different gate readout patterns, and
  drives the readout unit using the selected gate readout pattern, wherein the reader performs a first sampling action to hold a first output voltage after the each of the switch elements is in the non-conductive state, wherein the reader performs a second sampling action to hold a second output voltage after the each of the switch elements is in the conductive state, and wherein the gate readout pattern is defined by:
  at least one of a duration of the first sampling action, a duration of the second sampling action, and a duration of the conductive state of the each of the switch elements; and
  a gate period for repeating the readout of the signal value.

13. A non-transitory storage medium storing a computer-readable program for a radiographic imaging device, the radiographic imaging device comprising:
  a first hardware processor;
  a sensor that includes multiple semiconductor elements arranged two-dimensionally and multiple switch elements respectively connected to the semiconductor elements;
  a gate driver that causes each of the switch elements of the sensor to switch between a conductive state and non-conductive state so as to release charge from each of the semiconductor elements; and
  a reader that performs readout of a signal value according to an amount of the charge released by the each of the semiconductor elements of the sensor, wherein the program causes the first hardware processor of the radiographic imaging device to:
  set an imaging condition that affects a dose of radiation reaching the sensor;
  select a gate readout pattern according to the set imaging condition among different gate readout patterns; and
  drive the gate driver and the reader using the selected gate readout pattern, wherein the program causes the reader to perform a first sampling action to hold a first output voltage after the each of the switch elements is in the non-conductive state, wherein the program causes the reader to perform a second sampling action to hold a second output voltage after the each of the switch elements is in the conductive state, and wherein the gate readout pattern is defined by:
  at least one of a duration of the first sampling action, a duration of the second sampling action, and a duration of the conductive state of the each of the switch elements; and
  a gate period for repeating the readout of the signal value.

* * * * *